United States Patent [19]

Kouge

[11] Patent Number: 4,857,656
[45] Date of Patent: Aug. 15, 1989

[54] ACTIVE ESTERS USED FOR PRODUCTION OF ESTERS OR AMIDES AND PROCESS FOR PRODUCING ESTERS OR AMIDES

[75] Inventor: Katsushige Kouge, Yamaguchi, Japan

[73] Assignee: Sanshin Kagaku Kogyo Co., Ltd., Yanai, Japan

[21] Appl. No.: 23,251

[22] Filed: Mar. 9, 1987

[51] Int. Cl.$^4$ ............................................. C07C 69/96
[52] U.S. Cl. ..................................... 558/271; 558/20; 558/56; 560/142
[58] Field of Search .................... 558/20, 56, 271; 560/142

[56] References Cited

U.S. PATENT DOCUMENTS 3,392,186  7/1968  Lynn ................................ 558/20

OTHER PUBLICATIONS

E. Fisher, Chem. Ber., 36, 2094–2106 (1903).
Th. Curtius, Chem. Ber., 35, 3226–3228 (1902).
H. G. Khorana, J. Chem. Soc., 1952, 2081–2088.
Th. Wieland et al., Justus Liebigs Annalen der Chemie, 569, 117–121 (1950).
M. Bodanszky et al., J. Amer. Chem. Soc., 81, 5688–5691 (1959).
J. Kovacs, M. Q. Ceprini, Chemistry & Industry, 1965, 2100.
G. W. Anderson et al., J. American Chem. Soc., 85, 3039 (1963).
Japanese Patent Application OPI No. 166670/1985 (Chem. Abst. 104, 88559p) (1986).
Chem. Abstr., 103, 196393t (1985).
Preliminary Lecture Draft–52nd Annual Meeting of the Japanese Chemical Association.
Kouge et al., Chem. Express, 1986, 1(7), 427–30 (C.A. 106–119,381x (1987).

*Primary Examiner*—Nicky Chan
*Attorney, Agent, or Firm*—Sandler & Greenblum

[57] ABSTRACT

This invention is characterized by synthesizing an active ester represented by the general formula

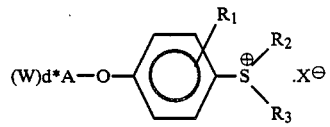

using an active esterifying agent consisting of a sulfonium salt represented by the general formula

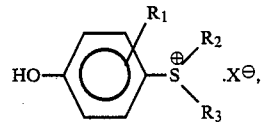

and further reacting the above-said active ester with a nucleophilic agent represented by the general formula H—B—Y to produce an ester or amide represented by the general formula (W)d.A—B—Y.

1 Claim, No Drawings

ACTIVE ESTERS USED FOR PRODUCTION OF ESTERS OR AMIDES AND PROCESS FOR PRODUCING ESTERS OR AMIDES

FIELD OF THE INVENTION AND DESCRIPTION OF RELATED TECHNOLOGIES

This invention relates to an active esterifying agent and active ester thereof used for chemical synthesis of peptides, chemical modification of proteins and production of other esters and amides useful in industries and a process for producing esters or amides using said active ester.

For a chemical synthesizing process of physiologically active peptides such as favoring peptides typified by many peptidic hormones and sweetenings, a chemical modification process of proteins which is the chemical means for immune response, elucidation of enzymatic functions or transformation of proteins, and also a chemical synthesizing process of other esters or amides useful in industries, various methods have been studied for a long time. For example, a method using acid chlorides [E. Fischer, Chem. Ber., 36, 2094–2106 (1903)], a method using acid azides [J. Curtius, Ber., 35, 3228 (1902)], a method using dehydrating condensing agents such as dicyclohexylcarbodiimide (H. G Khorana, J. Chem. Soc., 1952, 2081–2088), a mixed acid anhydride method [Th. Wieland et al., Justus Liebigs Annalen der Chemie, 569, 117–121 (1950)], and an active ester method to promote nucleophilic substituting reaction by transforming carboxyl components to the active esters [M. Bodauszky et al., J. Amer. Chem. Soc., 81, 5688 (1959); J. Kovacs, M. Q. Ceprini, Chemistry and Industry, 1965, 2100: G. W. Anderson et al., J. Amer. Chem. Soc., 85, 3039 (1963): Japanese Patent Application OPI No. 16670/1985 (Chem. Abst. 104, 88559p] have been known.

For formation of a carboxylic acid amide bond, particularly, in these various methods, the active ester method, differing from other methods, has a characteristic in which the reaction proceeds even when water is present in the reaction system, and is also an important reaction reagent in the field of chemical modification of proteins, as well as synthesis of peptides.

Namely, the active ester method means a process for producing an amide ($RCONHR'$) or an ester ($RCOOR'$) by reacting an organic compound ($RCOOH$) with an active esterifying assistant ($X-OH$) to form an active ester ($RCOOX$) and then causing an amine ($R'NH_2$) or an alcohol ($R'OH$) to act on this active ester, and has an advantage in which the reaction proceeds under relatively mild conditions.

As the active esters conventionally used for such purposes, esters with phenol derivatives such as paranitrophenol and pentachlorophenol and esters with N-hydroxysuccinimide have been known. Namely, the reaction system of aminolysis, for example, by means of the active ester process is as follows,

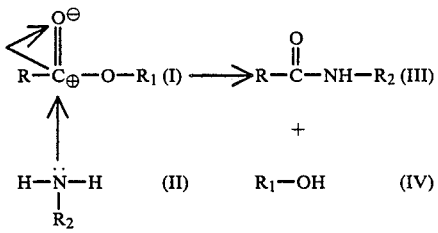

In an active ester (I), generally, R activates the carbonyl carbon using a phenyl nucleus having an electrophilic group, for example, p-nitrophenyl or pentachlorophenyl. After completion of aminolysis, a hydroxyl compound (IV), the unreacted active ester (I) and an amine component (II) are naturally present as a mixture in the formed product (III). To take out only the desired product (III) from this state, each of (I), (II), and (IV) is required to be removed out of the reaction system. Generally, this mixture is dissolved in an organic solvent having no compatibility with water such as ethyl acetate. (II) is first removed by separating and washing the solution using a diluted acidic aqueous solution, and then removing procedures of (IV) and (I) are started. With respect to removal of (IV), separation and washing using a minutely alkaline aqueous solution is generally conducted, but a complete removal can not be achieved as the active ester (I) has a high hydrophobicity when $R_1$ is a phenyl nucleus. Accordingly, to obtain a satisfactory purity, removal by recrystallization or chromatographic purification is required. Furthermore, for removal of (I), only recrystallization by an organic solvent is effective, as (I) is hardly dissolved in water. However, when the active ester (I) and the product (III) are similar in solubilities, (I) can not be completely removed, which often causes reduction of purity. Thus, as active esters more easily purified, hydroxyamide systems, for example, N-hydroxysuccinimide, is considered to be effective. However, although it has a merit in which, as N-hydroxysuccinimide is water-soluble in itself, it is easily removed by washing with water, the unreacted active esters (I) are not water-soluble in general, and thus, its removal must depend on recrystallization by organic solvents. Also, in this case, as the solubility is more similar to that of the product (III), compared with the case of phenol type active esters, a satisfactory result can not be obtained for reaction yields in total. On the other hand, when the amine component which is an attacking reagent for forming a carboxylic acid amide bond is a high molecular peptide and protein, the use of water is required, as the solvent for the amine component. However, in the reaction using each of the above-said reagents, as the active ester is hardly soluble to water, it must be dissolved and reacted in a mixed system of a solvent having a compatibility with water and, consequently, the amine component is inevitably deformed by the solvent.

OBJECT AND SUMMARY OF THE INVENTION

An object of this invention is to provide an active esterifying assistant for solubilizing an active ester to water and a novel water-solubilized active ester.

Another object of this invention is to provide a producing process in which an ester or amide can be produced by proceeding the active ester method moderately in water by using the water-solubilized active ester.

Among the sulfonium compounds of this invention represented by the general formula

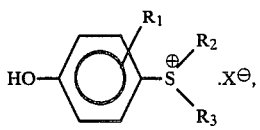

4-hydroxy-2-methylphenyldimethylsulfonium iodide is a public-known compound described in J. Amer. Chem. Soc., 80, 3425 (1958) and has been known as a water-soluble phenol derivative having a high acidity. However, there have been no examples of deriving this compound to the ester and also reporting its function as the active ester.

The active esterifying agent of this invention is a water-soluble compound from its Ionicity and properties of the substituting groups. Therefore, in separation and removal after reaction which has been regarded as a problem in the conventional active esters, it has also a characteristic in which it can be easily separated and removed from the desired product by washing with water. As the active esters of this invention themselves are water-soluble in most cases, a system of water alone can be selected as the reaction solvent, even when amino acids, peptides and proteins which are water-soluble compounds are used as the nucleophilic agent. This is an important characteristic which is not possessed by the conventional active esters, and can become a means to solve the problem of deformation by organic solvents. Also, in synthesis of esters and amides in a system using general organic solvents, there is no difference in reaction yields between the active esters of this invention and the conventional active esters.

With respect to reactivity, the active esters of this invention afford reaction yields equal or more, compared with the conventional esters of paranitrophenol, pentachlorophenol and N-hydroxysuccinimide.

Furthermore, a significant characteristic of the active esters of this invention is that they are water-soluble, and thus the reaction can be conducted in a solvent of water alone. This enables an easy reaction of compounds in vivo such as amino acids, peptides, and proteins in aqueous solutions under moderate conditions which was conventionally impossible. Conventionally, when such reaction was conducted, functional groups and side chains not participating in the reaction were required to be protected by proper protective groups before conducting the reaction, but in the water-soluble active ester of this invention, as water is used as the reaction solvent, a fixed group of the main chains, side chains and functional groups is protonated and substantially protected, and as a result, only α-amino groups of amino acids or only terminal amino groups of peptides can be selectively acylated as the main chains, side chains and functional groups remain not protected. In the case of chemical modification of proteins, as organic solvents are not employed, it has an excellent action in which deformation is never caused which is not possessed by the conventional active esters.

The active esters of this invention are not limited only by using water as the reaction solvent, and even if other general solvents having a compatibility with water or solvents having no compatibility with water are employed, they exhibit the effect sufficiently. For example, in two layer heterogenerous system of chloroform, dichloromethane or ethyl acetate which can dissolve the esters of this invention and water, the reaction also proceeds smoothly.

Also, the active esters of this invention can be applied to not only formation of carboxylic acid amide bonds but also synthesis of other esters or amides useful in industries.

DETAILED DESCRIPTION OF PREFERRED EMBODIMENT OF THE INVENTION

The active esterifying agent of esters or amides of this invention comprises a sulfonium salt represented by the general formula

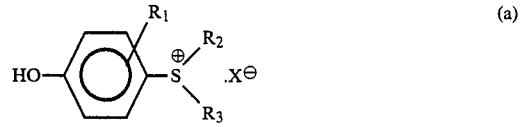

(a)

wherein $R_1$ represents a hydrogen, an alkyl group, a halogen group, a nitro group, or an alkoxy group; $R_2$ and $R_3$, which may be same or different, each represents an alkyl group; and $X^{\ominus}$ represents an anion typified by a halogen ion, a perchloric acid ion, a hydrogensulfuric acid ion, a methylsulfuric acid ion, and a p-toluenesulfonic acid ion.

The preferred concrete examples of the active esterifying agent include 4-hydroxyphenyldimethylsulfonium perchlorate, 4-hydroxyphenyldimethylsulfonium p-toluenesulfonate, 4-hydroxyphenyldimethylsulfonium methylsulfate, 4-hydroxyphenyldimethylsulfonium hydrogensulfate and the like.

The active ester derived from these active esterifying agents of esters or amides comprises an ester sulfonium salt represented by the general formula

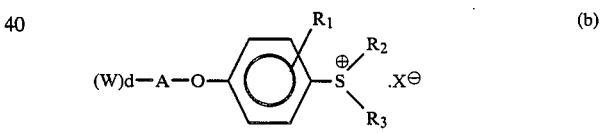

(b)

wherein A represents —CO—, —SO$_2$—, >PO—, or >PS— groups, $R_1$–$R_3$ and $X^{\ominus}$ are the same defined in the above general formula (a); and for W and d,
1. when the above-said A is a divalent group, d is 1 and W represents an alkyl group, an alkenyl group, an alkynyl group, a cycloalkyl group, an alkyl group of $C_1$–$C_5$ substituted by 1–3 halogen atoms, a group

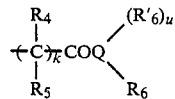

(wherein $R_4$ and $R_5$, which may be same or different, each represents a hydrogen, a hydroxyl group, a mercapto group, an alkyl group or an aryl group; when Q is oxygen or sulfur, U is 0, and $R_6$ represents a hydrogen, an alkyl group, an aryl group, a cycloalkyl group, an alkenyl group, an alkynyl group, or an aralyl group; when Q is nitrogen, u is 1, and $R_6$ and $R'_6$, which may be same or different, each represents a hydrogen, an alkyl group, an alkenyl group, an alkynyl group, an aryl group, or an aralkyl group; and k represents an integral number of 1-4), an alkoxy group, a cycloalkoxy, group, an aryl group, an aryloxy group, a aralkoxy group represented by

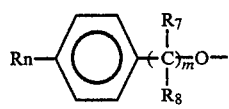

(wherein Rn represents a hydrogen, a halogen atom, an alkyl group, an alkoxy group, an alkylthio group, an alkylsulfonyl group, an aryl group, or a

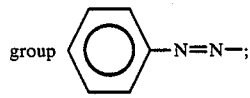

$R_7$ and $R_8$, which may be same or different, each represents a hydrogen or an alkyl group; and m represents an integral number of 1-4), a isobonyloxy group, a furfuryloxy group, a fluorenylmethoxy group, or a group $R_9.R_{10}N$— (wherein $R_9$ and $R_{10}$, which may be same or different, each represents a hydrogen, an alkyl group, an alkenyl group, an alkynyl group, an aryl group, and aralkyl group, or $R_9$ and $R_{10}$ may be combined each other to form a ring having 3-6 carbon atoms, when occasion demands, containing other hetero atoms), and when the above-said A is particularly

W may be an amino acid group in which a proper protective group is introduced or not introduced in the α-amino group and/or the side chain together with W—CO—, and/or a group of a peptide or protein, and
2. when the above-said A is a trivalent group, d is 2 and, in this case, two WS, which may be same or different, each represents an alkoxy group, an alkenoxy group, an alkyl group, an aralkoxy group, an aryloxy group, an alkylamino group, an alkylthio group, or an aryl group.

The present active ester can be easily synthesized by reaction of a p-(dialkylsulfonio)phenol of the active esterifying agent represented by the above-mentioned general formula (a) with an acid chloride represented by $R_4$—CO—Cl (wherein $R_4$ represents an alkyl group, a halogenoalkyl group, a tert-butyloxy group, a benzyloxy group, a methoxybenzyloxy group, a phenyl group, or a fluorenylmethoxy group), p-toluenesulfonyl chloride or diphenylphosphinothionyl chloride, or by action of dicyclohexylcarbodiimide with $R_4$—COOH.

The active ester represented by the general formula

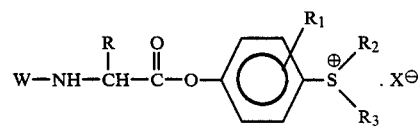

can be easily synthesized by reacting a p-(dialkylsulfonio)phenol of the active esterifying agent represented by the above-said general formula (a) with an amino acid derivative represented by the general formula

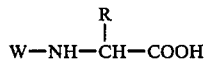

wherein W represents a hydrogen atom or a protective group of α-amino group of an amino acid, R represents an amino acid side chain having or not having a protective group, and $R_1$-$R_3$ and $X^\ominus$ are the same as defined in the above general formula (a),
by means of the mixed acid anhydride method, or by condensing them under action of dicyclohexylcarbodiimide.

When a proper nucleophilic agent represented by the general formula H—B—Y is acted (reacted) on the active ester derived from the thus synthesized phenol sulfonium salt [ester sulfonium salt; represented by the above general formula (b)] as the substrate, peptide derivatives, chemical modified products of proteins, or other esters and amides represented by the general formula $$(W)_d.A\text{—}B\text{—}Y \qquad (e)$$

can be easily obtained in high yield and high purity.

In the above general formula H—B—Y, B represents $NR_{11}$ (wherein $R_{11}$ represents a hydrogen, an alkyl group, an alkenyl group, an alkynyl group, or an aryl group), oxygen or sulfur, and Y represents a group represented by

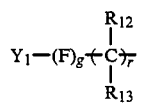

(wherein $Y_1$ represents a hydrogen, an alkyl group, a cycloalkyl group, a halogenoalkyl group, or an aryl group; F represents NH, oxygen, sulfur, alkylimino, or NHCO groups; $R_{12}$ and $R_{13}$, which may be same or different, each represents a hydrogen, HO—, HS—, an alkyl group, an akylthio group, an alkylamino group, an alkenyl group, an alkynyl group, or an aryl group; g is 0 or 1; and r represents an integral number of 0-4), or H—B—Y is an amino acid in which a proper protective group is introduced or not introduced in the side chain and/or the α-carboxyl group, a peptide or protein in which a proper protective group is introduced or not introduced in the side chain and/or the terminal carboxyl group, or a glucide in which the hydroxyl group in the molecule is properly protected or not protected.

The reaction of the active ester (ester sulfonium salt) represented by the above general formula (b) with the nucleophilic agent represented by the above general formula H—B—Y is conducted in water alone, in an organic solvent having a compatibility with water alone, in a mixed system of the above two, or in two phase system of a solvent having no compatibility with water or a solvent having a compatibility with water and water.

This invention is further illustrated in more detail by examples, but the compounds of this invention and the utility thereof are not limited only by the decribed examples.

SYNTHETIC EXAMPLE 1

Synthesis of p-dimethylsulfoniophenylbenzylcarbonate methylsulfate

In 20 ml of acetonitrile was dissolved 2.6 g of p-dimethylsulfoniophenol methylsulfate, and 1.6 ml of benzyloxycarbonylchloride and 1.4 ml of triethylamine were drop-wise added thereto under stirring at room temperatuare. The reaction mixture was filtered to remove the deposited triethylamine hydrochloride. The filtrate was concentrated under reduced pressure and the residue was crystallized by adding ether.

Yield: 3.8 g (95%).
m.p.: 76°–80° C.
IR: 1760 cm$^{-1}$ (C=O).
Elem. anal. value: C, 51.33%; H, 5.11%; S, 15.91%, (Theoretical value): C, (51.01)%; H, (4.99)%; S, (15.99)%.

SYNTHETIC EXAMPLE 2

Synthesis of 4-dimethylsulfonio-2-methylphenylbenzylcarbonate perchlorate

In 30 ml of acetonitrile was dissolved 2.68 g of 4-dimethylsulfonio-2-methylphenol perchlorate, and 1.6 ml of benzyloxycarbonylchloride and 1.4 ml of triethylamine were dropwise added thereto under stirring at room temperature. The reaction mixture was filtered to remove the deposited triethylamine chloride. The filtrate was concentrated under reduced pressure and the residue was crystallized by adding ether.

Yield: 3.5 g (91%).
m.p.: 129°–133° C.
IR: 1760 cm$^{-1}$ (C=O).
Elem. anal. value C, 49.37%; H, 4.15%; S, 8.31%; (Theoretical value) C, (49.45)%; H, (4.37)%; S, (8.24)%.

SYNTHETIC EXAMPLE 3

Synthesis of p-dimethylsulfoniophenylacetate methylsulfate

In 30 ml of acetonitrile was dissolved 2.6 g of p-dimethylsulfoniophenol methylsulfate, and 0.8 ml of acetyl chloride and 1.4 ml of triethylamine were dropwise added thereto. The reaction mixture was filtered to remove the deposited triethylamine hydrochloride. The filtrate was concentrated under reduced pressure and the residue was crystallized by adding ether.

Yield: 2.8 g (92%).
m.p.: 84°–86° C.
IR: 1760 cm$^{-1}$ (C=O).
Elem. Anal. Value: C, 42.54%; H, 4.99%; S, 21.05%; (Theoretical value): C, (42.87)%; H, (5.19)%; S, (20.81)%.

SYNTHETIC EXAMPLE 4

Synthesis of t-butyloxycarbonylphenylalanine p-dimethylsulfoniophenyl ester methylsulfate In 80 ml of acetonitrile were dissolved 2.65 g of t-butyloxyphenylalanine and 2.66 g of p-dimethylsulfoniophenol methylsulfate, and dicyclohexyl carbodilmide was added thereto with stirring under ice-cooling. The reaction mixture was further stirred for 2 hours under ice-cooling and for 1 hour at room temperature, and then the dicyclohexyl urea was filtered off. The filtrate was concentrated under reduced pressure and the residue was crystallized by adding ether. This crystalline product (hygroscopicity) gave 1 spot by TLC.

Yield: 4.3 g (84%).
IR: 1680 cm$^{-1}$ (C=O).
Rf: 0.51 (Butanol:Water:Pyridine:Acetic acid 4:1:1:2).

SYNTHETIC EXAMPLE 5

Benzyloxycarbonylalanine p-dimethylsulfoniophenyl ester methylsulfate

In 20 ml of acetonitrile was dissolved 2.24 g of benzyloxycarbonylalanine. After cooling the reaction mixture to −5° C., 1.4 ml of triethylamine was added, and further 1 ml of ethyl chloroformate was dropwise added thereto. After 10 minutes, 50 ml of acetonitrile solution of 2.66 g of p-dimethylsulfoniophenyl ester methylsulfate was gradually added thereto. The reaction mixture was stirred at 0° C. for 2 hours and then at room temperature for 8 hours. The resulting reaction mixture was filtered, the filtrate was concentrated under reduced pressure, and the residue was crystallized by adding ether. This crystalline product (Hygroscopicity) afforded 1 spot by TLC.

Yield: 3.7 g (78%).
IR: 1680 cm$^{-1}$ (C=O).
Rf: 0.50 (Butanol:Water:Pyridine:Acetic acid 4:1:1:2).

WORKING EXAMPLE 1

(Acylating reaction in aqueous solution) Synthesis of benzyloxycarbonylglycine

In 20 ml of water was dissolved 4.0 g of p-dimethylsulfoniophenylbenzylcarbonate methylsulfate prepared in Synthetic Example 1, and 20 ml of an aqueous solution of 0.75 g of glycine and 1.4 ml of triethylamine was dropwise added thereto under stirring at room temperature. The reaction mixture was further stirred for 8 hours at room temperature and adjusted to pH 2 by adding 2% HCl. The aqueous solution was extracted twice with 50 ml of ethyl acetate. The ethyl acetate layer was dried and concentrated under reduced pressure, and ether was added to the obtained residue to afford a white crystalline product.

Yield: 1.78 g (85.0%).
m.p.: 119°–120° C. (Literature value 120° C.).

WORKING EXAMPLE 2

(Acylating reaction in aqueous solution)

Synthesis of N-acetylphenylalanine

In 30 ml of water was dissolved 3.1 g of p-dimethylsulfoniophenylacetate methylsulfate prepared in Synthetic Example 3, and 20 ml of an aqueous solution of 1.64 g of phenylalanine and 1.4 ml of triethylamine was dropwise added thereto under stirring at room temperature. The reaction mixture was further stirred for 12 hours at room temperature and adjusted to pH 2 by adding 2% HCl. The aqueous solution was extracted twice with 50 ml of ethyl acetate. The ethyl acetate layer was washed with water, dried, and concentrated under reduced pressure, and ether was added to the obtained residue to afford a white crystalline product.

Yield: 1.4 g (70%).
m.p.: 167°–168° C. (Literature value 168° C.).
[α]D: +42° (Literature value +47°).

WORKING EXAMPLE 3

(Acylating Reaction in Aqueous Solution)

Synthesis of benzyloxycarbonylarginine

In 30 ml of water was dissolved 4.0 g of p-dimethylsulfoniophenylbenzylcarbonate methylsulfate prepared in Synthetic Example 1, and 20 ml of an aqueous solution of 1.74 g of arginine was dropwise added thereto under stirring at room temperature. The reaction mixture was further stirred for 10 hours at room temperature and then cooled to 5° C. to deposit white crystals. The crystalline product was filtered and washed with water to obtain the desired product.

Yield: 2.3 g (75%).
m.p.: 174°–175° C. (Literature value 175° C.).

WORKIING EXAMPLE 4

(Acylating reaction in aqueous solution)

Synthesis of benzyloxycarbonylalanylglycine

In 20 ml of water was dissolved 4.33 g of p-dimethylsulfoniophenylbenzylcarbonate methylsulfate prepared in Synthetic Example 1, and 20 ml of an aqueous solution of 0.68 g of glycine and 1.28 ml of triethylamine was dropwise added thereto under stirring at room temperature. The reaction mixture was stirred for 12 hours at room temperature and adjusted to pH 2 by adding 2% HCl. The aqueous solution was extracted twice with 100 ml of ethyl acetate. The ethyl acetate layer was dried and concentrated under reduced pressure, and ether was added to the obtained residue to afford white crystals.

Yield: 1.58 g (61.9%).
m.p.: 134.1°–135.3° C.
[α]D: −17.5° (cl. Alc).

WORKING EXAMPLE 5

(Synthesis of peptide in aqueous solution)

Synthesis of Benzyloxycarbonylphenylalanylproline

In 30 ml of water was dissolved 5.47 g of benzyloxycarbonylphenylalanine p-dimethylsulfoniophenyl ester methylsulfate obtained by a synthesizing method according to Synthetic Example 5, and 20 ml of an aqueous solution of 1.15 g of proline and 1.4 ml of triethylamine was dropwise added thereto under stirring. The reaction mixture was further stirred for 12 hours at room temperature, adjusted to pH 2 by adding 2% HCl, and extracted twice with 50 ml of ethyl acetate. The ethyl acetate layer was washed with water, dried, and concentrated under reduced pressure, and the obtained residue was recrystallized by adding ether. This crystalline product indicated only the peak of the desired product by HPLC.

Yield: 3.25 g (82%).
m.p.: 105°–106° C. (Literature value 106° C.).
[α]D: −63° (Literature value −64°).

WORKING EXAMPLE 6

(Synthesis of peptide in aqueous solution)

Synthesis of Benzyloxycarbonylalanylvaline

In 30 ml of water was dissolved 4.72 g of benzyloxycarbonylalanine p-dimethylsulfoniophenyl ester methylsulfate obtained by to Synthetic Example 5, and 20 ml of an aqueous solution of 1.17 g of valine and 1.4 ml of triethylamine was dropwise added thereto under stirring. The reaction mixture was stirred overnight at room temperature, adjusted to pH 2 by adding 2% HCl, and extracted twice with 50 ml ethyl acetate. The ethyl acetate layer was washed with water, dried, and concentrated under reduced pressure, and the residue was recrystallized by adding ether. This crystalline product indicated only the peak of the desired product by HPLC.

Yield: 2.6 g (81%).
m.p.: 123°–124° C. (Literature value 121°–124° C.).
[α]D: −12° C. (Literature value −12° C.).

WORKING EXAMPLE 7

(Synthesis of peptide in aqueous solution)

Synthesis of t-butyloxycarbonylmethionylarginylphenylalanylamide

In 20 ml of water was dissolved 2.01 g of arginylphenylalanylamide hydrochloride, and this aqueous solution was adjusted to pH 7.4 by adding triethylamine. To the reaction mixture was dropwise added 5 ml of an aqueous solution of 2.5 g of t-butyloxycarbonylmethionine p-dimethylsulfoniophenyl ester methylsulfate under stirring at room temperature, and the reaction mixture was maintained at pH 7.4 for 2 hours. As an oil was deposited from the reaction mixture, this oil was extracted with 50 ml of ethyl acetate. The ethyl acetate layer was washed with water, dried and then concentrated under reduced pressure, and the obtained residue was crystallized by adding ether. This crystalline product gave 1 spot by TLC and also indicated a positive Sakaguchi reaction. When this was hydrolyzed using 6N HCl and analyzed by means of an amino acid analyzer, Met:Arg:Phe was 1:1.01:0.99, respectively.

Yield: 3.47 g (65%).
m.p.: 84°–85° C.
[α]D: −21° (Literature value −21°).

WORKING EXAMPLE 8

(Reaction in two layer system of chloroform-water)

Synthesis of benzyloxycarbonylalanylvaline

In 50 ml of chloroform was dissolved 4.14 g of benzyloxycarbonylalanine p-methylsulfoniophenyl ester p-toluenesulfonate, and 20 ml of an aqueous solution of 0.91 g of valine and 1.1 ml of triethylamine was dropwise added thereto under stirring at room temperature. The reaction mixture was stirred for 8 hours at room temperature and then separated. The chloroform layer was washed with water, dried, and concentrated under reduced pressure, and ether was added to the residue to afford white crystals.

Yield: 2.42 g (75.0%).
m.p.: 121.5°–124.2° C.
[α]D: −12.0° C. (cl. Alc).

WORKING EXAMPLE 9

(Reaction in homogeneous mixed solvent of acetonitrile-water)

Synthesis of tosylphenylalanine

In 50 ml of acetonitrile was dissolved 4.08 g of p-toluenesulfonyl p-dimethylsulfoniophenyl ester perchlorate, and 50 ml of an aqueous solution of 1.65 g of phenylalanine and 1.4 ml of triethylamine was dropwise added thereto under stirring at room temperature. The reaction mixture was stirred for 5 hours and adjusted to pH 2 by adding 2% HCl to deposit white crystals. The crystals were filtered and recrystallized from 60% alcohol to afford the desired product.
Yield: 2.08 g (85.0%).
m.p.: 133.5°–135.1° C.

WORKING EXAMPLE 10

Synthesis of ε-benzyloxycarbonyllysine

A pH electrode was put in a solution in which 14.6 g of lysine was dissolved in 100 ml water, and 60 g (1.5 mol equivalent against lysine) of p-dimethylsulfoniophenylbenzylcarbonate methylsulfate synthesized in Synthetic Example 1 was added thereto under stirring at 20° C. As the pH became lowered as the reaction proceeded, 1M sodium carbonate solution was dropwise added thereto so as to make pH 8.0. While pH was maintained at 8.0 for 4 hours, the deposited white crystals were filtered, washed with water and methanol successively, and dried to afford 19.6 g (70% of the theoretical value) of the desired product.
m.p.: 255° C. (Literature value m.p. 253°–255° C.).
$[\alpha]D$: +14° (cl, 1N—HCl; Literature value +14.4°).

WORKING EXAMPLE 11

Synthesis of δ-benzyloxycarbonylornithine

A pH electrode was put in a solution in which 16.9 g of ornithine hydrochloride was dissolved in 100 ml of water, and 60 g (1.5 mol equivalent against ornithine) of p-dimethylsulfoniophenylbenzylcarbonate methylsulfate synthesized in Synthetic Example 1 was added thereto under stirring at 20° C. The pH of the reaction system was maintained at 8.0 by 1N-NaOH and the reaction mixture was reacted for 4 hours. The deposited crystals were filtered, washed with water and methanol successively, and dried to afford 20.7 g (78% of the theoretical value) of the desired product.
m.p.: 250°–3° C. (Literature value 253°–5° C.).
$[\alpha]D$: +12° (cl, 1N-HCl; Literature value +13.1°).
The presence of dibenzyloxycarbonylornithine was not recognized in the obtained crystalline product by means of thin layer chromatography.

WORKING EXAMPLE 12

Synthesis of ε-tert-butyloxycarbonyllysine

A pH electrode was put in a solution of 14.8 g of lysine was dissolved in 100 ml of water, and 55 g (1.5 mol equivalent against lysine) of 4-tert-butyloxycarbonyloxyphenyldimethylsulfonium methylsulfate was added thereto under stirring at 20° C. The reaction was carried out at pH 8.0 according to the method of Working Example 10 to afford 17.7 g (72% of the theoretical value) of the desired product.
m.p.: 250°–255° C. (Literature value 237°–255° C.)
$[\alpha]D$: +6° (cl, 2N—NH₄OH; Literature value +4.7°).
The presence of di-tert-butyloxycarbonyllysine was not recognized in the obtained crystalline product by means of thin layer chromatography.

REFERENCE EXAMPLE 1

(Reaction in two layer system of chloroform-water using p-nitrophenyl ester)

Synthesis of benzyloxycarbonylglycine

In 50 ml of chloroform was dissolved 2.73 g of p-nitrophenylbenzyloxy carbonate, and 20 ml of an aqueous solution of 0.75 g of glycine and 1.4 ml of triethylamine was dropwise added thereto under stirring at room temperature. The reaction mixture was stirred for 8 hours at room temperature and then separated. The chloroform layer was washed with 1N aqueous ammonia and water, dried, and concentrated under reduced pressure, and ether was added to the obtained residue to crystallize the desired product. The yield was 0.12 g and only 10% of the theoretical amount was obtained.

REFERENCE EXAMPLE 2

(Suspending reaction in water using ester of N-hydroxysuccinimide)

Synthesis of benzyloxycarbonylglycine

In 50 ml of water was suspended 2.5 g of N-(benzyloxycarbonyloxy)succinimide, and the suspension was stirred for 1 hour at room temperature. To this suspension was added 20 ml of an aqueous solution of 0.75 g of glycine and 1.4 ml of triethylamine, and the reaction mixture was stirred for 12 hours as it was, but the desired product, benzyloxycarbonylglycine, could not be obtained.

REFERENCE EXAMPLE (According to the conventional technology)

In 320 ml of hot water was dissolved 11 g of lysine hydrochloride. To this was added 24 g of basic copper carbonate, and the reaction mixture was boiled for 10 minutes and filtered as it remained hot. The filtrate was allowed to cool, and 10 g of sodium hydrogencarbonate and 12 ml of benzyloxycarbonylchloride were divided into four, each of which was added thereto every 10 minutes. After stirring for 3 hours, the precipitate was filtered and washed with water and ethanol successively. Then the precipitate was dispersed in 250 ml of water and dissolved by 6N-HCl, and hydrogen sulfide was passed thereto for 1 hour. After filtering the deposited copper sulfide, the filtrate was washed with 1N—HCl, and then the hydrogen sulfide was removed by passing air to the resulting filtrate. The thus obtained solution was adjusted to pH 6.5 by conc. aqueous ammonia under ice-cooling, and the deposited crystalline product was filtered, washed with water and ethanol successively, and dried to afford 11.5 g (68% of the theoretical value) of the desired product.

[EFFECT OF THE INVENTION]

The active esters of this invention are useful active esters with respect to acylating reagents and synthesis of peptides, as apparent from Working Examples and Reference Examples, and are proved to have excellent properties which are not possessed by the conventional active esters.

Also, in separation and removal after reaction, the active esters of this invention can be easily separated and removed from the desired product by washing with water, and afford a reaction yield equal or more, compared with the conventional active esters.

What is claimed is:

1. An ester represented by the general formula:

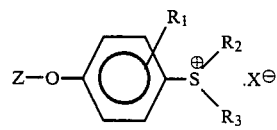

wherein Z represents a group represented by $R_4$—CO—, wherein $R_4$ represents a member selected from the group consisting of a tert-butyloxy group, a benzyloxy group, a p-methoxybenzyloxy group, and a fluorenyl-methoxy group; $R_1$ represents a member selected from the group consisting of a hydrogen, an alkyl group, a halogen group, a nitro group and an alkoxy group; $R_2$ and $R_3$ each represents an alkyl group selected from the group consisting of the same alkyl group and different alkyl groups; and $X^-$ represents an anion selected from the group consisting of a halogen ion, a perchloric acid ion, a hydrogensulfuric acid ion, a methylsulfuric acid ion, and a p-toluenesulfonic acid ion.

* * * * *

UNITED STATES PATENT AND TRADEMARK OFFICE
CERTIFICATE OF CORRECTION

PATENT NO. : 4,857,656
DATED : August 15, 1989
INVENTOR(S) : Katsushige KOUGE

It is certified that error appears in the above-identified patent and that said Letters Patent is hereby corrected as shown below:

At column 1, line 18, change "favoring" to ---flavoring---.

At column 1, line 28, change "3228" to ---3226-3228---.

At column 1, line 37, change "Bodauszky" to ---Bodanszky---.

At column 1, line 42, change "16670/1985" to ---166670/1985---.

At column 3, line 20, change "lonicity" to ---ionicity---.

At column 4, line 65, change "aralyl" to ---aralkyl---.

At column 5, line 2, delete "," after "cycloalkoxy".
At column 5, line 3, change "a" to ---an---.
At column 5, line 13, insert ---group--- after "a".
At column 5, line 17, delete "group" before " -n=n-".
At column 5, line 28, insert ---to--- before "each".
At column 5, line 42, change "WS" to ---Ws---. At column 5, line 55, change "diphenylphosphlnothionyl" to ---diphenylphosphinothionyl---.

At column 6, line 14, change "nucleophillc" to ---nucleophilic---.

At column 6, line 23, change "(∅)" to ---(e)---.

At column 6, line 44, change "akylthlo" to ---alkylthio---.

At column 6, line 67, change "decribed" to ---described---.

At column 7, line 9, change "temperatuare" to ---temperature---.

UNITED STATES PATENT AND TRADEMARK OFFICE
CERTIFICATE OF CORRECTION

PATENT NO. : 4,857,656

DATED : August 15, 1989

INVENTOR(S) : Katsushige KOUGE

It is certified that error appears in the above-identified patent and that said Letters Patent is hereby corrected as shown below:

At column 7, line 15, change "$cm^{311}$" to ---$cm^{-1}$---.

At column 7, line 63, change "carbodilmide" to ---carbodiimide---.

At column 11, line 45 of the printed patent, change "14.8" to ---14.6---.

At column 14, line 2, change "X-" to ---$X^-$---.

At the front page, left column of the printed patent the foreign priority data is missing.

Signed and Sealed this

Twenty-third Day of June, 1992

Attest:

DOUGLAS B. COMER

Attesting Officer

Acting Commissioner of Patents and Trademarks